United States Patent [19]

Korn

[11] Patent Number: 4,637,796
[45] Date of Patent: Jan. 20, 1987

[54] OFFICE FABRICATED, ADJUSTABLE FUNCTION REGULATOR

[76] Inventor: Marcel Korn, 502 Lindell Ave., Leominster, Mass. 01453

[21] Appl. No.: 704,958

[22] Filed: Feb. 25, 1985

[51] Int. Cl.⁴ .............................................. A61C 7/00
[52] U.S. Cl. ...................................................... 433/7
[58] Field of Search ........................................ 433/6, 7

[56] References Cited

U.S. PATENT DOCUMENTS 4,433,956  2/1984  Witzig ..................................... 433/7

Primary Examiner—Robert Peshock

[57] ABSTRACT

This invention is a removable orthodontic therapy appliance adapted to be assembled and modified by an orthodontist without laboratory assistance, into a function regulator adapted to correct malocclusions of the teeth. It is a device of component parts of different sizes comprising: buccal shield base assemblies, buccal shelf extension assemblies, bicuspid - cuspid extension assemblies, a lip-pad, lingual roller assembly unit, a labial bow assembly and connecting means adapted to connect said assemblies into a function regulator. The invention provides an improved means for positioning the function regulator relative to the patient's dental arch, and it may be used in conjunction with band therapy. The invention reduces treatment costs, promotes patient cooperation during treatment, and permits the use of simultaneous fixed appliance therapy. In one embodiment of the invention it can be used primarily to promote positioning and or growth of the mandibular arch. A further advantage of the appliance of this invention is that it may be readily modified as treatment progresses.

12 Claims, 11 Drawing Figures

OFFICE FABRICATED, ADJUSTABLE FUNCTION REGULATOR

BACKGROUND OF THE PRIOR ART

This invention is directed to the field of orthodontics, i.e., the correction of malocclusions of the teeth and jaws. Two basic methods of orthodontics include fixed band therapy and removable appliance therapy (functional).

In the fixed band therapy method, appliances known as brackets are rigidly attached to the patient's teeth, and are interconnected to each other by an archwire. The archwire is formed into a predetermined shape by the orthodontist to apply force to the teeth to move them into proper relation to each other.

Two treatment methods are generally recognized in the fixed band therapy method, i.e., the "Begg" or lightwire treatment method, and the "Edgewise" treatment method. Such fixed band appliances may be used to correct malocclusions in children and adults. They may be used in conjunction with auxilliary aids such as headgears, elastics, etc., to apply the desired corrective force or forces.

In the second therapy method, a removable appliance is used which is designed to promote the development of the dental arch such that the teeth assume a proper positional relationship relative to each other with or without the simultaneous use of fixed band appliances. This therapy is generally only useful in the treatment of children, and is less often used in the treatment of adults or those with teeth in the permanent dentition.

An important appliance in the removable appliance therapy mehtod was developed by Dr. Rolf Frankel of Zwickau, East Germany. Dr. Frankel termed his appliance a "function regulator" and that term in used to describe the object of this invention since it is an improvement on his device. The Frankel function regulator is a one-piece, removable appliance designed to promote proper dental arch development and jaw relationship during periods of facial or dental arch development. It is laboratory fabricated upon instruction by the orthodontist. The Frankel function regulator is described in the text: Graber, T. M. and Neuman, B.: *Removable Orthodontic Appliances;* The Frankel Appliance, Chapter 15, p. 526–565, W. B. Saunders Company, Philadelphia (1977). Pages 526–565 of this text are incorporated by reference into this specification.

The Frankel function regulator, although an important orthopedic treatment device, has disadvantages which the present invention overcomes. The Frankel device must be laboratory fabricated, which involves several patient visits to the orthodontist for model preparation and fitting. It is of one-piece construction and hence it cannot be adjusted to any appreciable extent as patient treatment progresses. The conventional Frankel appliance's position in the patient's oral vestibule is maintained relative to the maxillary dental arch by transdental wires (palatal and protrusion bow) which are positioned in contact grooves which are cut between the teeth. This cutting of contact grooves, i.e., inter-proximal discing is not required with the appliance of this device.

SUMMARY OF THE INVENTION

This invention is directed to a removable orthodontic-orthopedic therapy appliance which comprises individual elements which may be assembled by an orthodontist into a function regulator without laboratory assistance. It is an appliance which is optionally assembled from the following elements: a buccal shield base assembly; a bicuspid—cuspid extension assembly; a buccal shelf extension assembly; a lip-pad lingual roller assembly unit, a labial bow connector and connecting means adapted to join said assemblies into a function regulator and position said device relative to the patient's dental arch. The function regulator of this invention is connected to headgear tubes affixed to molar bands which are attached to the maxillary molars to establish and maintain its posterior position relative to the maxillary arch; the anterior position being established by the labial bow and lip-pad, linqual roller assembly unit.

The individual elements of the invention are fabricated in a number of different sizes so that the orthodontist may select the appropriate size of each element to assembly a function regulator of the correct dimensions to fit the patient's dental arch and treatment needs. In the appropriate case, one or more of said assemblies may be deleted, e.g., in a case where only mandibular repositioning is required, the lip-pad lingual roller assembly unit may be attached directly to the headgear tube—molar bands with suitable connecting means. This assembly of individual elements can be used to achieve mandibular advancement in a patient or to stabilize the mandibular position in an adult being treated for temporo mandibular joint syndrome.

The buccal shield base assembly, bicuspid—cuspid extension assembly, buccal shelf extension assembly and lip-pad lingual roller assembly unit are preferably interconnected by adjustable connecting means such as adjustable orthodontic skeleton screws which are well known in the art. Similarly the buccal shield base assemblies may be adapted to receive palatal expansion devices such as a transpalatal bar.

In this invention posterior maxillary positioning of the appliance is accomplished by the use of headgear tubes affixed to molar bands on the patient's posterior molars. This method of positioning provides many advantages. The attachment is more rigid and precise than transdental (palatal bow, protrusion bow) wires and vertical stop wires found in the conventional Frankel function regulator. The appliance is more comfortable because its bulk is reduced and it fits better. There is no need to cut contact grooves between the patient's teeth to make room for the palatal bow and protrusion bow or to provide maxillary positioning points. The elimination of these transdental wires allows access to the dentition so that concurrent dental corrections with fixed appliances can be accomplished while at the same time functional objectives are achieved. Access to the dentition allows the orthodontist to simultaneously use fixed band therapy in order to accomplish dental movement of the teeth.

The lip-pad, roller assembly unit of the appliance of this invention represents a major improvement in comfort and tissue adaptation over the lingual shield and lip-pads of the conventional Frankel appliance. Experience has shown that the contact points of the lingual shields and lip-pads of the conventional Frankel function regulator are the location of sore spots in the patient's tissue and a significant factor in poor or reduced cooperation by the patient. Reduction in tissue trauma by the replacement of those elements of the conven-

DESCRIPTION OF THE PREFERRED EMBODIMENTS

This invention is that of a removable orthodontic therapy appliance designed to correct abnormal muscle function that causes abnormal jaw and dental arch relationships. It is an improvement on the conventional Frankel function regulator which is well known in the field of orthodontics. The use, design and other aspects of the Frankel function regulator is described in the text: Removable Orthodontic Appliances cited supra in this specification. The reader is referred to pages 526–565 of this text for a more detailed explanation of the Frankel function regulator. In summary, the device is designed to remove restricting muscle pressure to promote the development of the alveolar arches and to promote muscle and tissue development where needed. This invention is described in terms of the Frankel FR II function regulator. However, it will be apparent to one of ordinary skill to use this invention for the construction of other forms of a Frankel function regulator.

FIG. 1–FIG. 4 represent various views of a conventional FR II, Frankel function regulator. These drawings are presented for reference purposes. In these and other drawings of this specification, the same elements located on opposite sides of the appliance are given the same reference number.

FIG. 5–FIG. 9 represent various views of a comparable function regulator of this invention.

Figure 10:
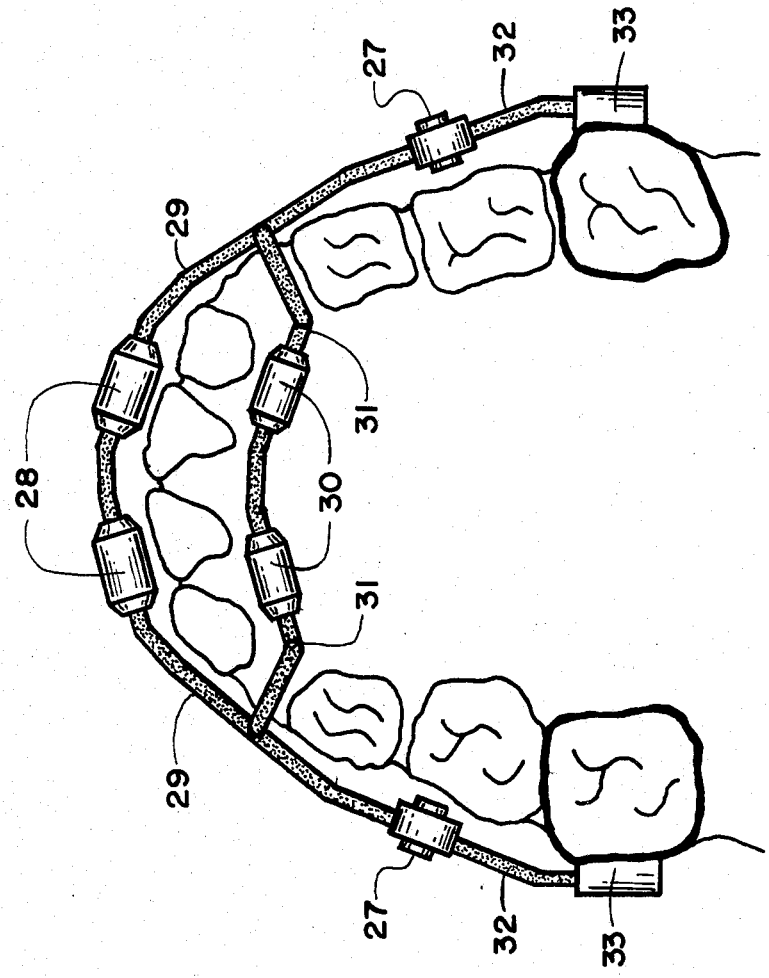
FIG. 10 is a top view of a simplified function regulator of this invention which functions to advance the mandible.
Figure 11:
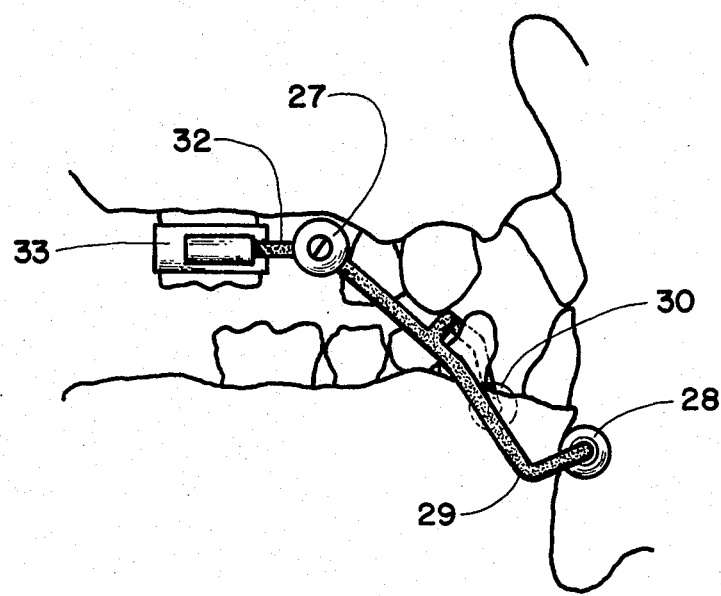
FIG. 11 is a side view of a simplified function regulator of this invention.

FIG. 10–FIG. 11 represent the side and top view of one simplified version of a function regulator of this invention. This invention is that of a system of prefabricated elements of various sizes that may be assembled into a function regulator having improved treatment capability and an improved means for positioning the function regulator in the oral vestibule.

Figure 1:
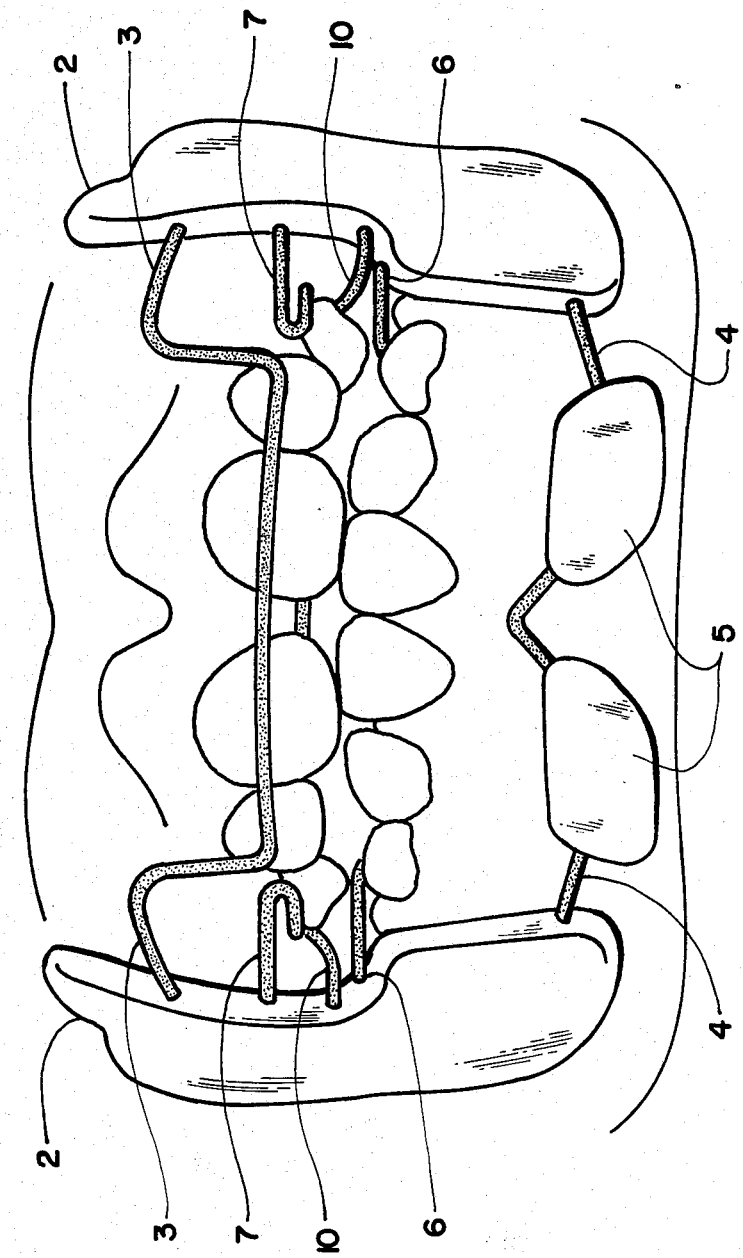
FIG. 1 is a front perspective view of a conventional Frankel function regulator.
Figure 2:
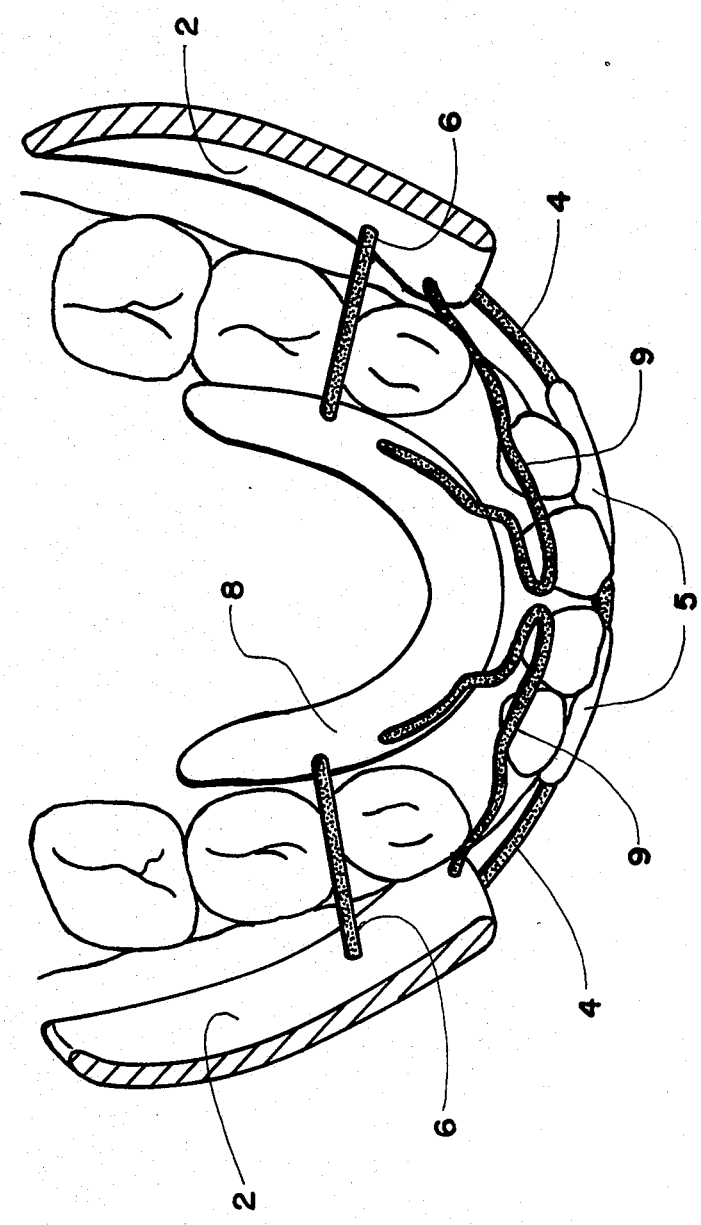
FIG. 2 is a top sectional view of a conventional Frankel function regulator relative to the mandibular (lower) dental arch.
Figure 3:
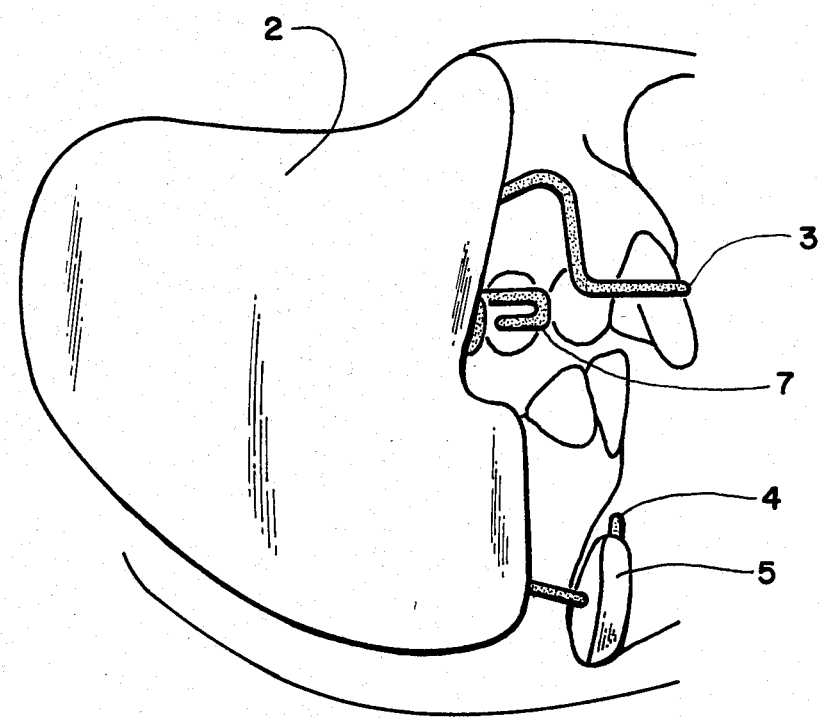
FIG. 3 is a side view of a conventional Frankel function regulator.
Figure 4:
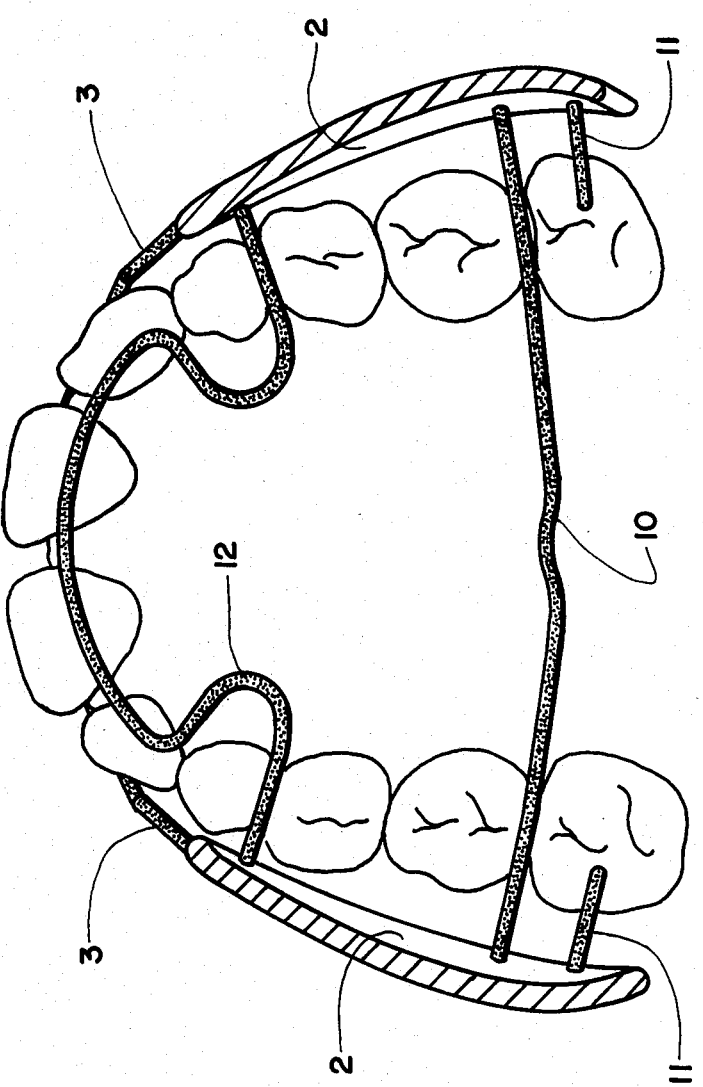
FIG. 4 is a bottom sectional view of a conventional Frankel function regulator relative to the maxillary (upper) dental arch.

FIG. 1 is a front view of a conventional Frankel function regulator 1 positioned in the patient's mouth. It is a one-piece laboratory-fabricated appliance that is constructed by reference to models and instructions provided to the laboratory by the orthodontist. These models and instructions are developed by the orthodontist based on one or more office visits. The various elements of the appliance are cast in acrylic or some other suitable material and connecting means permanently embedded in the acrylic members to form an integral one-piece device incapable of being adjusted to any appreciable extent as treatment progresses.

The conventional Frankel function regulator appliance consists of two buccal shields 2 designed to protect the buccal surfaces of the posterior teeth and the corresponding alveolar structures from restricting pressures emanating from the buccinator muscle. The buccal shields 2 are anteriorally connected by a labial bow 3 and lip-pad connector wires 4. The lip-pad connector wires 4 support two lip-pads 5 which eliminate or reduce pressure exerted by the mentalis muscle. Similar in function to the buccal shields 2, the lip-pads 5, promote alveolar bone development. They also function in conjunction with lingual shield 8 and lingual springs 9 (see FIG. 2) to position the mandible in the desired mesial position. The lingual shield connector wires 6 support the lingual shield 8 and add lateral rigidity to the appliance. Two cuspid guide loops 7 support the appliance against the mesial surfaces of the cuspids. The palatal bow 10, molar vertical stop wires 11 and the protrusion bow 12 of the Frankel function regulator are more easily seen in FIG. 4. The palatal bow 10 connects the buccal shields 2 and it functions to position the appliance relative to the maxillary arch and adds rigidity to the appliance. Correct maxillary positioning of the appliance is accomplished by cutting contact grooves (1–1.5 mm in depth) between the first molars and the second premolars. The palatal bow rests in these grooves against the mesial surface of the first molars. The vertical stop wires 11 prevent the appliance tipping or dropping into the vestibular fold The protrusion bow 12 is similarly positioned in contact grooves cut between the cuspids and bicuspids. It positions the appliance anteriorly in the maxillary arch and it stabilizes the appliance in the transdental direction.

Figure 5:
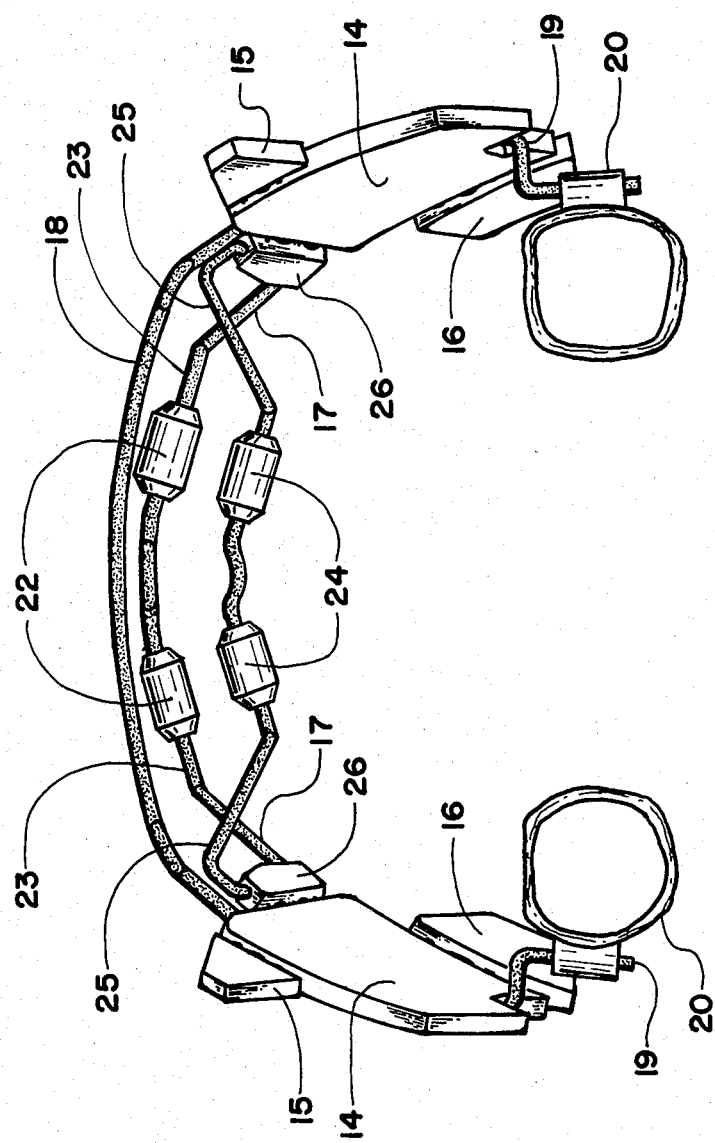
FIG. 5 is a top perspective view of the function regulator of this invention.

FIG. 5–FIG. 9 illustrate the comparable FR II type function regulator of this invention. FIG. 5 illustrates a top perspective view of this appliance. It comprises: two buccal shield base assemblies 14, two bicuspid-cuspid extension assemblies 15, two buccal shelf extension assemblies 16, one lip-pad, lingual roller assembly unit 17, a labial bow 18, and connecting means adapted to join said elements into a function regulator and to position said function regulator in the oral vestibule.

Referring still to FIG. 5, the appliance is posteriorly positioned in the patient's mouth by demountably attaching two molar insert rods 19 to molar band-headgear tubes 20 affixed to the patient's molars. Any suitable method may be used to attach the molar insert rods 19 to the buccal shield base assemblies 14. Preferably the anterior end of said rods 19 are threaded and screwed into threaded female sleeves (not shown) which are molded into said base assemblies 14. The position of said assemblies and said rods is fixed by means of lock nuts (not shown). The posterior ends of said rods are positioned in the tubes of the headgear tube-molar band means 20. Alternatively, threaded posterior ends of said rods and lock nuts (not shown) may be used for the attachment.

It is readily apparent that the anterior-posterior position of the appliance of this invention may be adjusted during fitting of the appliance or during treatment by changing the length of said rods or adjusting their length or by changing the said roller assembly unit. This posterior attachment method provides a more precise attachment means than that employed in the conventional Frankel function regulator, it is adjustable as treatment progresses, it eliminates the need to cut positioning grooves in the teeth and the need for a palatal bow 10 of the conventional appliance which is used in the conventional device to provide transdental stability.

Figure 6:
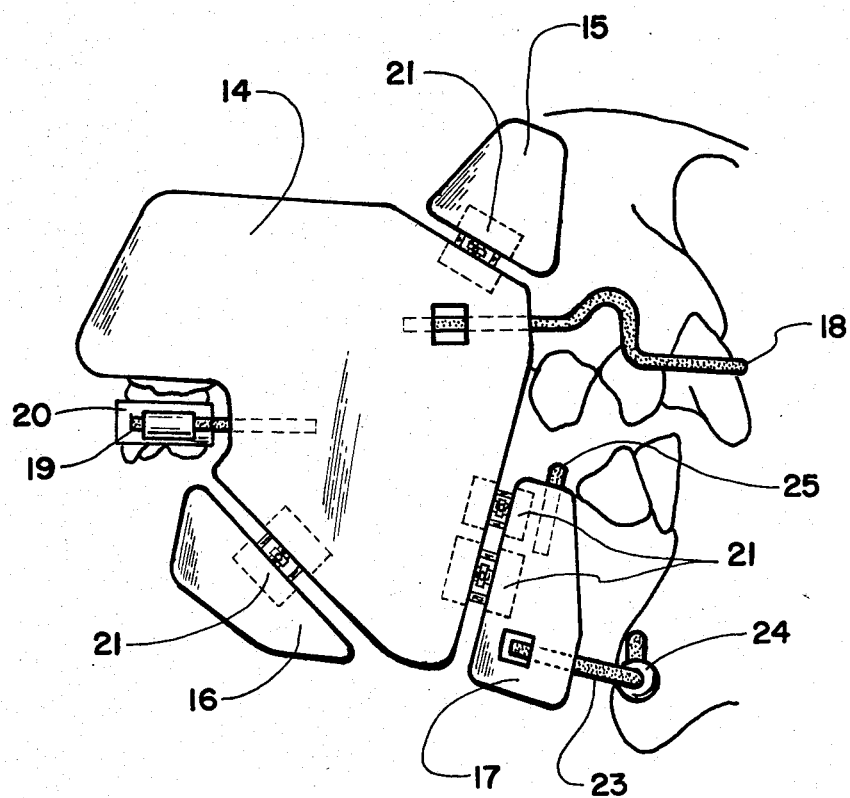
FIG. 6 is a side view of the function regulator of this invention.

Referring to FIG. 6, the bicuspid-cuspid extenion assemblies 15, buccal shelf extention assenblies 16 and the lip-pad, lingual roller assembly unit 17 are connected to the buccal shield assemblies 14 by adjustable connecting means 21. The adjustable connecting means 21 may be well known skeleton screw means. These adjustable connection means 21 may be affixed intially to either the buccal shield assemblies 14 or to the attachable extension assemblies and lip-pad, lingual roller assembly unit, preferably to the said extension assemblies and roller assembly unit.

The lip-pad, lingual roller assembly unit 17 is illustrated in FIG. 5 and FIG. 6. It comprises two labial lip-pad rollers 22, a labial roller connector wire 23, two lingual rollers 24, lingual roller connector wire 25, two lip-pad, lingual roller assembly unit attachment plates 26 and adjustable connecting means 21 (see FIG. 6). The labial roller connector wire 23 may be rigidly fixed to said attachment plates 26 or adjustably connected to said plates 26 by constructing the labial roller connector wire with threaded ends adapted to be received in apertures in said plates and locked into position with lock nuts. The lingual roller connector wire 25 is preferably attached to said attachments plates 26 by molding it into said plates 26. However, the lingual roller connector wire 25 can be demountably attached to said plates. After selecting the appropriately sized lip-pad, lingual roller assembly unit, the practitioner may effect fine adjustment of said unit by either adjusting the length of the connector wires by the lock nut-threaded end attachment means or by bending said connecting wires. More significant adjustment of the lip-pad, lingual roller assembly unit 17 is effected by adjustment of the connecting means 21 to advance or retreat the unit relative to the mandibular arch.

The labial bow 18 is connected to the buccal shield base assemblies 14 by a threaded end portion and lock nut combination or by crimping and bending the ends of said bow after locating said ends in apertures formed in the buccal shield base assemblies 14.

Figure 7:
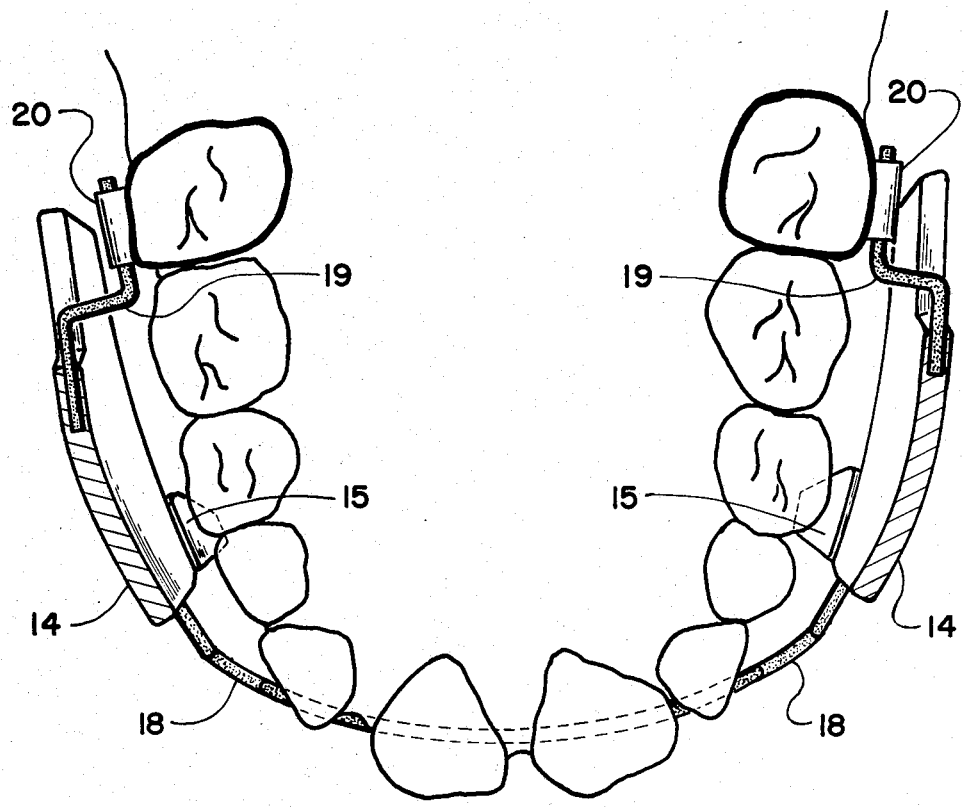
FIG. 7 is a bottom sectional view of the function regulator of this invention relative to the maxillary (upper) dental arch.
Figure 8:
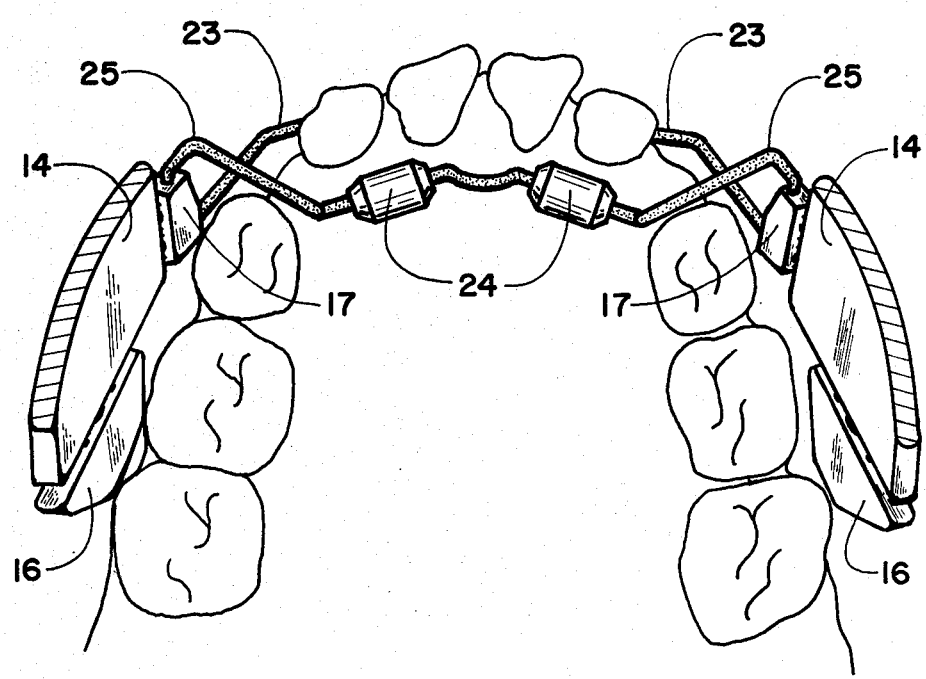
FIG. 8 is a top sectional view of the function regulator of this invention relative to the mandibular (lower) dental arch.
Figure 9:
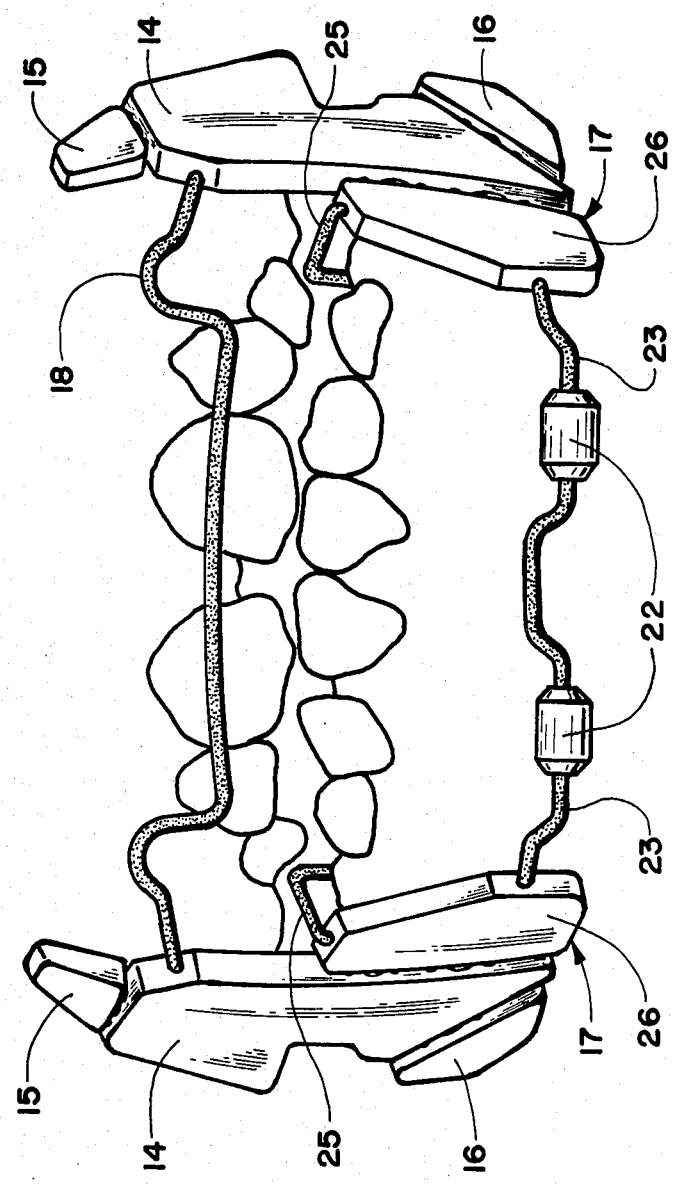
FIG. 9 is a front view of the function regulator of this invention.

FIG. 7 shows a maxillary sectional view of the appliance of this invention. FIG. 8 is a mandibular sectional view and FIG. 9 shows a frontal view of the device positioned in the oral vestibule.

In the practice of the invention, the basic elements of the deivce, i.e., buccal shield base assemblies 14, bicuspid-extension assemblies 15, buccal shelf extension assemblies 16, lip-pad, lingual roller assembly unit 17 and labial bow 18 would each be prefabricated in three to four sizes. The orthodontist would select the appropriately sized elements and assemble an appliance for the patient in one office visit. If the patient's condition warranted, one or more elements could be deleted or additional orthodontic appliances added to the device.

FIG. 10 and FIG. 11 illustrate a simplified function regulator of this invention.

This appliance is adapted to promote advancement of the mandibular arch or it may be used to stabilize its position relative to the temporo mandibular joint. The simplified function regulator of FIG. 10–FIG. 11 comprises molar insert rods 32, adapted to be demountably attached to headgear tubes 33 which are rigidly attached to bands 35 on the patient's maxillary molars. The molar insert rods 32 are posteriorally attached to a swivel joint connecting means 27. Anteriorally attached swivel joint connecting means 27 is a lingual roller-labial roller assembly unit 34 comprising a labial roller connecting wire 29 upon which are rotatably mounted labial rollers 28. Rigidly attached to the labial roller connecting wire is a lingual roller connector wire 31 upon which are rotatably mounted lingual rollers 30.

The swivel joint connecting means 27 is for illustration purpose shown as a separate element. However, in the preferred embodiment of this appliance the male and female portions of the swivel joint connecting means are integrally formed into the terminal ends of the molar insert rods 32 and the labial roller connecting wire 29, respectively.

In the practice of this embodiment of this invention, the molar insert rods 32 and the lingual roller-labial roller assembly unit 34 are fabricated in different sizes appropriate in length to assemble into an appliance adapted to fit the dental arch of patients of different sized facial structures. Five diffferent length rods and roller assembly units should be sufficient to fit the needs of the orthodontist. The orthodontist, from this selection of different sized elements would fabricate an appliance to suit the treatment needs of his patient and assemble the appliance and fit it to the patient at one office visit, without the need of laboratory assistance. The appliance may be modified as treatment progresses by changing the molar insert rods or the labial roller-lingual roller assembly unit or both. Secondly, the elements of appliances of this invention may be re-used after sterilization, which will result in an additional reduction in appliance costs.

Although my invention has been described in terms of specific embodiments, it should be understood that this description was for illustrative purposes and that my invention is not limited thereto since alternative embodiments within the scope of the appended claims will be apparent to one skilled in the art.

What I claim is:

1. An orthodontic function regulator adapted for demountable posterior attachment to the rear teeth of the maxillary arch and anterior positioning over the front teeth of the mandibular arch and further adapted for office assembly from a selection of prefabricated elements comprising:

A. Two buccal shield base assemblies adapted to receive and connect said elements of said regulator;

B. A lip-pad, lingual roller assembly unit, said unit being generally "U" shaped and adapted at its anterior, closed end to be positioned over the front teeth of the mandibular arch, said assembly having rotatably mounted thereon labial roller means and lingual roller means adapted to be positioned labially and lingually respectively to the front teeth; said roler means being respectively mounted on generally "U"-shaped labial and lingual connector wires; the posterior ends of said wires being connected on each side of said assembly unit to an attachment plate; each of said plates being adapted to receive connecting means for demountably connecting said assembly unit to said base assemblies;

C. Connecting means for demountably connecting the posterior ends of said roller assembly unit to the anterior surface of said base assemblies;

D. Two base assembly connecting means adapted to demountably connect said base assemblies to the buccal surface of the rear teeth of the maxillary arch; wherein one of each of said base assemblies is connected to one of each of the posterior ends of said "U" shaped lip pad, lingual roller assembly unit and one of each of said base assembly connecting means is connected to the posterior surface of each of said base assemblies.

2. An orthodontic function regulator according to claim 1 further comprising at least one bicuspid-cuspid extension assembly and connecting means for demountably attaching said extension assembly to at least one buccal shield base assembly of said function regulator wherein said extension assembly is demountably connected to said base assembly.

3. An orthodontic function regulator according to claim 1 further comprising at least one buccal shelf extension assembly and connecting means for demountably attaching said shelf extension to at least one buccal shield base assembly of said function regulator wherein said shelf extension assembly is demountably connected to said base assembly.

4. An orthodontic function regulator according to claim 1 further comprising a labial bow connector and connecting means for demountably attaching said labial bow connector to and between the buccal shield base assemblies of said function regulator wherein said labial bow is demountably connected to and between said base assemblies.

5. An orthodontic function regulator according to claim 1 wherein said lip-pad, lingual roller assembly unit connecting means are adjustable in length.

6. An orthodontic function regulator according to claim 2 wherein said bicuspid-cuspid connecting means are adjustable in length.

7. An orthodontic function regulator according to claim 3 wherein said buccal shelf extension connecting means are adjustable in length.

8. An orthodontic function regulator according to claim 1 wherein said base assembly connecting means are demountable and adjustable in length.

9. An orthondontic function regulator according to claims 1, 2, 3, 4, 5, 6, 7, or 8 wherein the elements of said regulator are assembled from a selection of prefabricated elements.

10. A method of positioning and maintaining a function regulator as defined in claim 1 in therepeudic treatment position whereby the anterior position of said regulator is established and maintained in said position by means of a demountable lip pad, lingual roller assembly unit of said regulator positioned over the anterior alveolar portion of the mandibular arch and the posterior position of said regulator is established and maintained in said position by base assembly connecting means of said regulator demountably attached to the posterior molars of the maxillary arch.

11. An orthodontic function regulator adapted for demountable attachment to the rear teeth of the maxillary arch and for anterior positioning over the front teeth of the mandibular arch comprising:

A. a lingual-labial roller assembly unit having at least one anteriorally positioned labial roller rotatably mounted on a generally "U" shaped labial roller connecting wire member; at least one second posteriorally positioned lingual roller rotatably mounted on a lingual roller connecting wire member; said lingual roller connecting wire member being attached at each end to and positioned between said "U" shaped labial connecting wire member: said labial roller connecting wire member extending generally upwardly and posteriorally from said attachment points;

B. two molar-insert, rod members; one end of each rod member being adapted to be demountably attached to the buccal surface of opposing rear teeth; the other end of each of said rod members being adapted to be rotatably connected to one of each end of said "U" shaped labial roller connecting wire member; and C. two rotatably connecting means adapted to connect the posterior ends of said labial connecting wire member to anterior ends of said molar insert rod members;

wherein one of each rod member is rotatably attached to one of each of said ends of said "U" shaped labial roller connecting wire member.

12. A method of positioning and maintaining a function regulator as defined in claim 11 in therapeudic treatment position whereby the anterior position of said regulator is established and maintained in said position by means of a demountable lip pad, lingual roller assembly unit of said regulator positioned over the anterior alveolar portion of the mandibular arch and the posterior position of said regulator is established and maintained in said position by molar insert rods demountably attached to the posterior molars of the maxillary arch.

* * * * *